US00PP19900P2

(12) United States Plant Patent
Kordes

(10) Patent No.: US PP19,900 P2
(45) Date of Patent: Apr. 14, 2009

(54) ROSE PLANT NAMED 'KORTIFHAR'

(50) Latin Name: *Rosa hybrida*
Varietal Denomination: KORtifhar

(75) Inventor: Tim-Hermann Kordes, Offenseth-Sparrieshoop (DE)

(73) Assignee: W. Kordes' Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 378 days.

(21) Appl. No.: 11/505,092

(22) Filed: Aug. 15, 2006

(51) Int. Cl.
*A01H 5/00* (2006.01)

(52) U.S. Cl. ..... Plt./136
(58) Field of Classification Search ..... Plt./136, Plt./135, 132
See application file for complete search history.

(56) References Cited

PUBLICATIONS

QZ (CPVO) Application # 2005/1000 Jun. 1, 2005 European Union.

*Primary Examiner*—Kent L Bell

(57) ABSTRACT

A new and distinct variety of rose with long lasting, novel apricot colored flowers, and attractive foliage with good disease resistance. It exhibits uniform upright bushy growth habit with abundant flowers. The new variety propagates well using traditional methods. This new and distinct variety has shown to be uniform and stable in the resulting generations from asexual propagation.

2 Drawing Sheets

Latin name of genus and species: The botanical classification of the new rose plant is *Rosa hybrida.*

Variety denomination: The denomination of the new variety is 'KORtifhar'.

BACKGROUND OF THE INVENTION

The new variety of rose plant of the present invention originated from a controlled crossing in a breeding program of two distinct parents during the summer of 1994. The crossing was between, 'Macwairar' and 'KORtember'.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORtifhar'.

SUMMARY OF THE INVENTION

The new rose plant may be distinguished from its seed parent, Macwairar, by the following combination of characteristics:

1. The flowers of the seed parent are yellow, while the flowers of 'KORtifhar' are apricot colored; and
2. The flowers of the seed parent are very double, while the flowers of 'KORtifhar' are double.

The new rose plant may be distinguished from its pollen parent, 'KORtember' by the following combination of characteristics:

1. The flowers of the pollen parent are larger than the flowers of 'KORtifhar'; and
2. The flowers of the pollen parent are salmon pink, while the flowers of 'KORtifhar' are apricot colored.

The objective of the hybridization was to create a new and distinct rose plant with unique qualities, such as:

1. Compact and uniform growth and flowering;
2. Abundant attractive, recurrent flowers;
3. Attractive and abundant foliage; and
3. Resistance to diseases encountered in landscapes and gardens.

This combination of qualities is not present in prior rose cultivars. These objectives have been substantially achieved and in that distinguish 'KORtifhar' from all other varieties of which we are aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORtifhar' was selected in May, 1995 from the seeding beds to be asexually propagated for further evaluation. The first asexual propagation of 'KORtifhar' was done by budding to seedling understocks in August, 1995 at the W. Kordes Söhne Nursery in Offenseth-Sparrieshoop, Germany.

This initial and other subsequent propagations conducted in controlled environments show that the foregoing and all other characteristics of 'KORtifhar' come true to form and are transmitted through succeeding generations.

BRIEF DESCRIPTION OF THE DRAWING

The accompanying color illustration shows as true as is reasonably possible to obtain in color photographs of this type, the typical characteristics of the buds, flowers, leaves, and stems of 'KORtifhar'.

Specifically illustrated in SHEET ONE are developing flower buds, a half opened flower bloom, an open. flower, a dissected receptacle and detached sepals.

Specifically illustrated in SHEET TWO are a developing shoot tip, a section of a young stem, a section of a mature stem, and a single leave.

DETAILED BOTANICAL DESCRIPTION

The following is a description of 'KORtifhar', as observed growing in August, 2006 in a nursery in Jackson County, Oregon on plants of 3 years of age. Color references are made using The Royal Horticultural Society (London, England) Colour Chart, 2001 except where common terms of color are used.

For a comparison, several physical characteristics of the rose variety 'KORwarpeel', a rose variety from the same are compared to 'KORtifhar' in Chart 1.

CHART 1

| Characteristic | 'KORtifhar' | 'KORwarpeel' |
|---|---|---|
| Flower petals. | 25-30 petals. | 35 petals. |
| Petal size. | 30 mm long × 25 mm wide. | 40 mm long × 40 mm wide. |

Parents:

*Seed parent.*—'Macwairar'.

*Pollen/parent.*—'KORtember'.

Classification:

*Botanical classification.*—*Rosa hybrida,* 'KORtifhar'.

*Commercial classification.*—Hybrid Tea rose.

FLOWER AND FLOWER BUD

Blooming habit: Recurrent.

Flower bud:

*Size.*—Upon opening, 30 mm in length from base of receptacle to end of bud.

*Bud form.*—Long. Pointed ovoid.

*Bud color.*—As sepals first unfold, the bud color is a blend of Red Group 43C in the marginal zone, Yellow-Orange Group 20C in the middle zone, and Yellow Group 1B in the basal zone. When ¼ open, the upper surface of the petal is Orange Group N25B in the marginal and middle zones and Yellow Group 14A in the basal zone. When ¼ open, the lower surface of the petal is Orange Group 25B in the marginal and middle zone and Yellow-Orange Group 17C in the basal zone.

*Sepals.*—Size: Average 30–40 mm long×6–14 mm wide. Shape: Strong foliaceous appendages on three of the five sepals. Sepal apex is cirrose. Base is flat at union with receptacle. Quantity: Five. Surface texture: Inner side: Covered in fine hairs. Outer surface: Nearly smooth. Stipitate glands are present on the stipule margins. Color: Upper surface Green Group 138A Lower surface Green Group 137A. On sepals with foliaceous appendages, intonations of Greyed-Purple Group 183C.

Receptacle:

*Surface.*—With a limited number of fine hairs.

*Color.*—Green Group 138A.

*Shape.*—Funnel shaped.

*Size.*—7–8 mm (h)×8–9 nm (w).

Peduncle:

*Surface.*—With limited numbers of fine hairs.

*Length.*—50–60 mm average length.

*Diameter.*—2–2.5 mm average diameter.

*Color.*—Green Group 138A

*Strength.*—Moderately strong.

*Borne.*—Singly. 1–2 buds per flowering stem

Flower bloom:

*Fragrance.*—Light to moderate fresh floral scent.

*Duration.*—On the plant 6–8 days. Senesced petals drop away cleanly.

*Size.*—Medium flowered garden rose. Average flower diameter is 80–90 mm when open.

*Form.*—Shape of flower when viewed from the side: Upon opening, upper part: Convex. Upon opening, lower part: Convex. Open flower, upper part: Flattened convex. Open flower, lower part: Flat.

Color:

*Upon opening petals.*—Outermost petals: Outer Side: Green-Yellow Group 1B in the basal zone. Orange Group 28C in the marginal zone. Inner Side: Green-Yellow Group 1B in the basal zone and Orange Group 30A in the marginal zone. Innermost petals: Outer Side: Yellow-Orange Group 14A in the basal zone, Orange Group 30B in the middle zone, and Orange-Red Group N30C in the marginal zone. Inner Side: Yellow-Orange Group 14B in the basal zone, Orange Group 30B in the middle zone, and Orange-Red Group N30C in the marginal zone.

*Upon opening basal petal spots.*—Basal petal spot, outermost petals: Outer Side: Green-Yellow Group 1B. Inner Side: Green-Yellow Group 1B. Basal petal spot, innermost petals: Outer Side: Green-Yellow Group 14A. Inner Side: Green-Yellow Group 14A.

*After opening, petals.*—Outermost petals: Outer Side: Yellow-Orange Group 1C in the lower half of the petal and Orange Group 28B in the upper half of the petal. Inner Side: Yellow-Orange Group 1A in the lower half of the petal and Orange Group 28A in the upper half of the petal. Innermost petals: Outer Side: Yellow Group 12A in the basal zone and Orange Group 25C in the marginal and middle zone of the petal. Inner Side: Yellow-Orange Group 12A in the basal zone and Orange Group 30B in the marginal and middle zone of the petal.

*After opening, basal petal spots.*—Basal petal spot, outermost petals: Outer Side: Green-Yellow Group 9A. Inner Side: Green-Yellow Group 1A. Basal petal spot, innermost petals: Outer Side: Green-Yellow Group 12A. Inner Side: Green-Yellow Group 6A.

General Tonality: On open flower, a blend of Orange Group 30C and Orange Group 30D. No change in the general tonality at the end of the 4th day when the general tonality is a blend of Orange Group 28B and Orange Group N25C. Afterwards, tonality becomes Red Group 39B to Red Group 39C.

Petals:

*Petal count.*—Approximately 25–30 petals under normal conditions.

*Petal reflex.*—Petals reflex slightly.

*Petal edge.*—Nearly entire.

*Petal shape.*—Apex shape is round. Shape of base is acute.

*Petal size.*—30 mm long; 25 mm wide.

*Thickness.*—Average.

*Petal arrangement.*—Generally in a regular pattern with overlapping edges.

*Petaloids.*—Present. Average of 1–2 per flower. Petaloids are 10 mm long and 5–6 mm wide. Outer Side: Yellow-Orange Group 14A in the basal zone, Orange Group 30B in the middle zone, and Orange-Red Group N30C in the marginal zone. Inner Side:

Yellow-Orange Group 14B in the basal zone, Orange Group 30B in the middle zone, and Orange-Red Group N30C in the marginal zone. Surface texture is smooth. Shape is linear to elliptic.

Reproductive Organs:

*Pistils.*—Approximately 50 present. Stigmas: Location Superior in location to anthers. Color: Greyed-Green Group 195D. Styles: Length: 6 mm long. Color Green-White Group 157A. Intonations of Greyed-Purple Group 183C.

*Stamens.*—Average 60 in number. Anthers: Size: 3 mm long. Color: Yellow-Orange Group 14A. Pollen: Generally present. Color: Yellow-Orange Group 14A. Filaments: Color: Yellow-Orange Group 14A. Length: 6–7 mm.

THE PLANT

*Plant growth.*—Moderately vigorous. Upright to bushy. When grown as a budded nursery plant the average plant height is 80 cm and the average plant width is 40 cm.

*Stems.*—Stem color: Young wood: Green Group 138A. Older wood: Green Group 138A. Stem surface: Young wood: Smooth. Older wood: Smooth.

*Prickles.*—Present. Incidence: 3–4 per 10 cm of stem. Size: Average length: 4–5 mm. Color Immature prickles: Red Group 47C. Mature prickles: Greyed-Orange Group 176B. Senescing to Greyed-Orange Group 176B. On juvenile stems, entire prickle with intonations of Greyed-Purple Group 183C. Shape: Deeply concave.

*Leaves and leaflets.*—Normally 5 leaflets on normal leaves in middle of the stem. Leaf size: 120 mn (1)× 70–75 mm (w). Quantity: Average. Texture: Semi glossy. Smooth Color, mature foliage: Upper Leaf Surface: Green Group 137A. Lower Leaf Surface: Green Group 138A. Color, juvenile foliage: Upper Leaf Surface: Green Group 137A. Lower Leaf Surface: Green Group 138A.

*Stipules.*—Size: 12 mm (1) — 3–4mm (w). Stipule color: Green Group 138A. Presence of stipitate glands: Present on margins. Margins: Serrated.

*Petiole.*—Length: 15–20 mm. Diameter: 1.5 mm average. Petiole color: Green Group 138A. Anthocyanin present on juvenile tissue. Greyed-Purple Group 183C. Prickles: A few small prickles underneath. Stipitate glands: Limited numbers of stipitate glands on margins.

*Petiole rachis.*—Length: 40 mm Diameter: 1.0–1.25 mm. Color: Green Group 138A. Anthocyanin present on juvenile tissue. Greyed-Purple Group 183C. Margins: Glandular. Prickles: A few small prickles underneath. Stipitate glands: Limited numbers of stipitate glands on margins.

*Leaflets.*—Size: Average size of the terminal leaflet is 50–60 mm(l)×35 mm(w). Leaflet shape: Base: Ovate. Apex: Acute. Margins: Finely serrated. Texture: Medium (Hips/Seed formation: None observed.

Winter hardiness: To date, the variety has been grown successfully in Zone 5.

Disease resistance: Average resistance to powdery mildew, rust, and blackspot disease under normal growing conditions.

I claim:

1. A new and distinct variety of rose plant characterized by the following combination of characteristics:

(a) forms attractive, long lasting apricot colored flowers;

(b) exhibits uniform upright bushy growth habit;

(c) propagates well using traditional methods, and, (d) exhibits very good resistance to disease under normal growing conditions; substantially as herein illustrated and described.

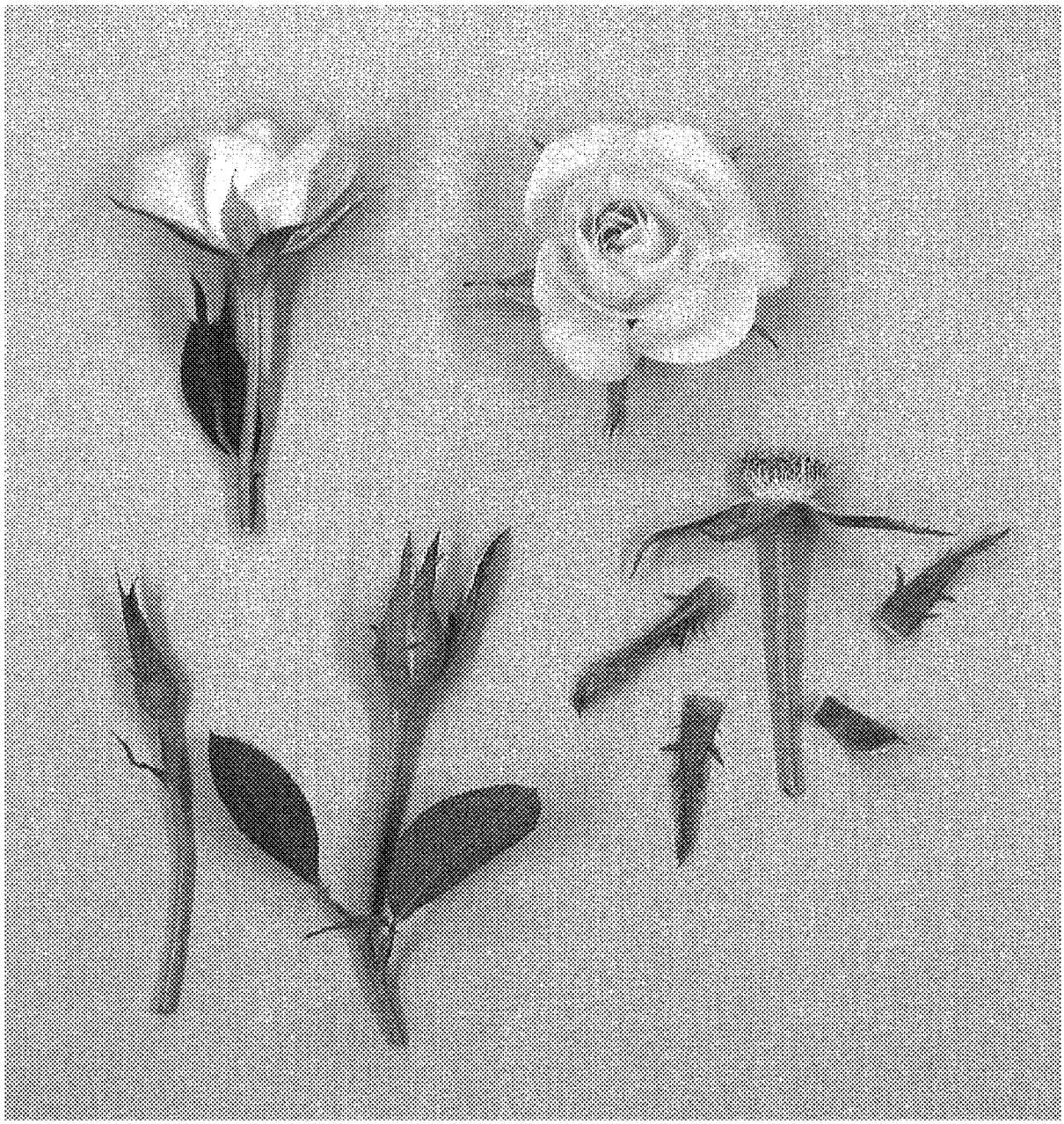

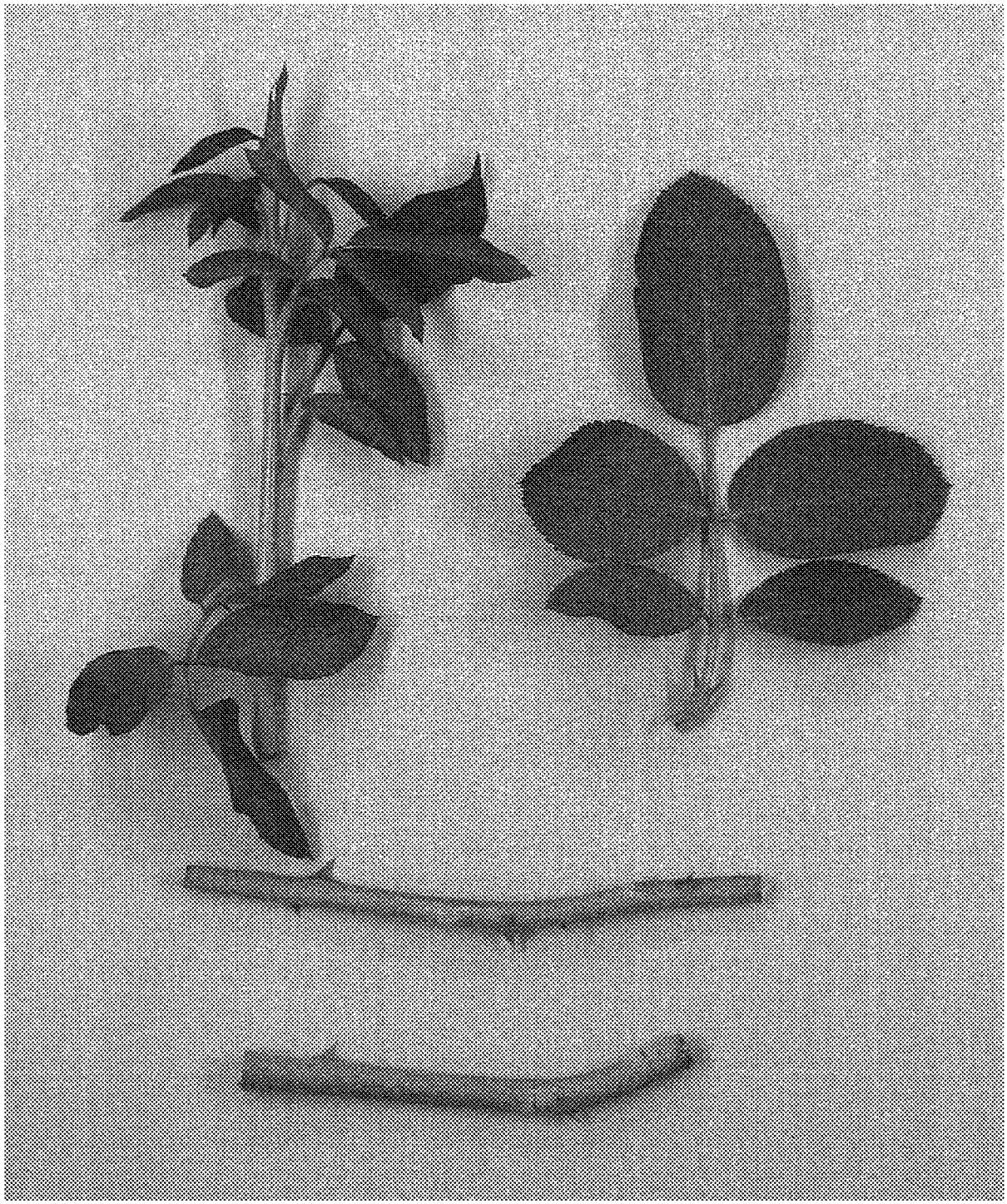

* * * * *